United States Patent
Komorowski et al.

(10) Patent No.: US 11,779,627 B1
(45) Date of Patent: Oct. 10, 2023

(54) CURCUMIN COMPOSITIONS AND METHODS OF USE AS AN NK3 ANTAGONIST

(71) Applicant: JDS Therapeutics, LLC, Harrison, NY (US)

(72) Inventors: James R. Komorowski, Trumbull, CT (US); Sarah Sylla, Brooklyn, NY (US)

(73) Assignee: JDS THERAPEUTICS, LLC, Harrison, NY (US)

( * ) Notice: Subject to any disclaimer, the term of this patent is extended or adjusted under 35 U.S.C. 154(b) by 0 days.

(21) Appl. No.: 18/205,792

(22) Filed: Jun. 5, 2023

Related U.S. Application Data

(62) Division of application No. 17/968,788, filed on Oct. 18, 2022.

(60) Provisional application No. 63/278,989, filed on Nov. 12, 2021.

(51) Int. Cl.
| | |
|---|---|
| *A61K 36/00* | (2006.01) |
| *A61K 36/9066* | (2006.01) |
| *A61P 15/12* | (2006.01) |
| *A61K 36/82* | (2006.01) |
| *A61K 31/26* | (2006.01) |

(52) U.S. Cl.
CPC .......... *A61K 36/9066* (2013.01); *A61K 31/26* (2013.01); *A61K 36/82* (2013.01); *A61P 15/12* (2018.01)

(58) Field of Classification Search
CPC ........................... A61K 36/82; A61K 36/9066
See application file for complete search history.

(56) References Cited

U.S. PATENT DOCUMENTS

| | | |
|---|---|---|
| 9,439,874 B2 | 9/2016 | Weng et al. |
| 11,090,287 B2 | 8/2021 | Bijno et al. |
| 2021/0220419 A1 | 7/2021 | Vieira et al. |
| 2021/0220422 A1 | 7/2021 | Parker |
| 2021/0275621 A1 | 9/2021 | Kim et al. |

FOREIGN PATENT DOCUMENTS

| | | | |
|---|---|---|---|
| EP | 2692352 A1 * | 2/2014 | ............. A61K 36/00 |

OTHER PUBLICATIONS

International Search Report and Written Opinion cited in PCT/US2022/047068, dated Jan. 3, 2023.
Shen et al, "Anti-ageing active ingredients from herbs and nutraceuticals used in traditional Chinese medicine: pharmacological mechanisms and implications for drug discovery," British journal of pharmacology, 2017; 174(11): pp. 1395-1425.
AAA Book—U.S. Department of Health & Human Services, Food & Drug Administration, "Guidance for Industry: Q3C Impurities: Residual Solvents," Dec. 1997 or its current issue.

* cited by examiner

*Primary Examiner* — Qiuwen Mi
(74) *Attorney, Agent, or Firm* — Arnall Golden Gregory LLP

(57) ABSTRACT

Disclosed herein are compositions for treating, ameliorating, preventing, or reducing the symptoms associated with menopause and/or hot flashes. The compositions disclosed herein comprise a curcumin composition, a green tea extract composition, and a phycocyanin composition that act as neurokinin 3 receptor antagonists. Also described herein are methods utilizing the aforementioned compositions.

8 Claims, 5 Drawing Sheets

CURCUMIN COMPOSITIONS AND METHODS OF USE AS AN NK3 ANTAGONIST

CROSS-REFERENCE TO RELATED APPLICATIONS

This application is a divisional of U.S. application Ser. No. 17/968,788, filed Oct. 18, 2022, which claims priority to U.S. Provisional Application No. 63/278,989 filed on Nov. 12, 2021, the disclosure of each of which is incorporated herein by reference in their entirety.

BACKGROUND

The neurokinin 3 (NK3) receptor is mainly expressed in the central nervous system and is the most selective of the tachykinin receptors, with highly preferential binding and activation by its endogenous ligand neurokinin-B (NKB). Research on the NK3 receptor, compared to the neurokinin-1 (NK1) and neurokinin-2 (NK2) receptors, has received little attention, in large part due to the absence of potent and selective non-peptide NK3 receptor antagonists. The inventors have identified a growing demand to develop novel NK3 receptor antagonists, because the inventors have identified the relationship between the NK3 receptor agonists and menopausal symptoms, which include hot flashes and night sweats. NK3 receptor antagonists are suspected to alleviate such symptoms. NK3 receptor antagonists are believed to confer many potential benefits to subjects, however the development of effective antagonists has eluded scientists in the prior art. As such, there is a need to develop and provide NK3 antagonists. By providing NK3 antagonists as pharmaceutical agents and/or dietary supplements, therapeutic and nutraceutical benefits can be realized, either individually, collectively, or in conjunction with other pharmaceutical agents and/or dietary supplements.

SUMMARY

Embodiments of the present disclosure relate to novel NK3 receptor antagonists and their use in the amelioration and/or treatment of menopause or symptoms associated therewith.

These and other features, aspects, and advantages of the present embodiments will become understood with reference to the following description, appended claims, and accompanying figures.

BRIEF DESCRIPTION OF THE DRAWINGS

FIG. 2 shows the hypothalamus levels of NKB for non-ovariectomized female Wistar rats (C); ovariectomized female Wistar rats (OVX); ovariectomized female Wistar rats treated with 600 mg human equivalent dose (HED) of a curcumin composition, as described herein (OVX+CL); ovariectomized female Wistar rats treated with 300 mg HED of a green tea extract composition, as described herein (OVX+EGCG); ovariectomized female Wistar rats treated with 100 mg HED of a phycocyanin composition, as described herein (OVX+P); and ovariectomized female Wistar rats treated with the combination of a curcumin composition, a green tea extract composition, and a phycocyanin composition, as disclosed herein, at the aforementioned dosages (OVX+CL+EGCG+P). The densitometric analysis of the relative intensity according to the control group of the western blot bands was performed with $\beta$-actin normalization to ensure equal protein loading. Blots were repeated at least three times (n=3) and a representative blot is shown. Data are presented as mean ± standard deviation. Different lowercase letters above data series (a-d) indicate a statistical difference between groups.

FIG. 3 shows the hypothalamus levels of NKB for a non-ovariectomized female Wistar rats (C); ovariectomized female Wistar rats (OVX); combination-treated ovariectomized female Wistar rats, wherein the treatment was 600 mg HED of a curcumin composition, 300 mg HED of a green tea extract composition, and 100 mg HED of a phycocyanin composition (OVX+CL1+EGCG1+P); combination-treated ovariectomized female Wistar rats, wherein the treatment was 450 mg HED of a curcumin composition, 450 mg HED of a green tea extract composition, and 100 mg HED of a phycocyanin composition (OVX+CL2+EGCG2+P); and combination-treated ovariectomized female Wistar rats, wherein the treatment was 720 mg HED of a curcumin composition, 180 mg HED a green tea extract composition, and 100 mg HED of a phycocyanin composition (OVX+CL3+EGCG3+P). The densitometric analysis of the relative intensity according to the control group of the western blot bands was performed with $\beta$-actin normalization to ensure equal protein loading. Blots were repeated at least three times (n=3) and a representative blot is shown. Data are presented as mean ± standard deviation. Different lowercase letters above data series (a-f) indicate a statistical difference between groups.

DETAILED DESCRIPTION

Figure 1A:
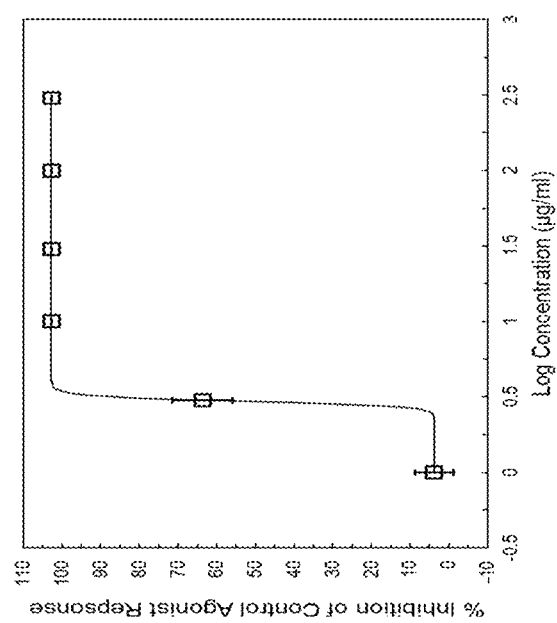
FIG. 1A shows the dose response curve of a curcumin composition, as described herein, which was administered to transfected Chinese Hamster Ovary (CHO) cells in vitro.

Some embodiments provide a composition comprising an amount of one or more curcumin extracts formulated as a curcumin composition. In certain embodiments, a curcumin composition can comprise an amount of diferuloylmethane, an amount of demethoxycurcumin (DMC), an amount of bis-demethoxycurcumin (BDMC), an amount of tetrahydrocurcumin, an amount of dihydrocurcumin, an amount of hexahydrocurcumin, an amount of octahydrocurcumin, or a combination of any of the foregoing. In some embodiments, a curcumin composition, as described herein, may comprise a pharmaceutically acceptable vehicle, carrier, or diluent.

Diferuloylmethane is depicted below:

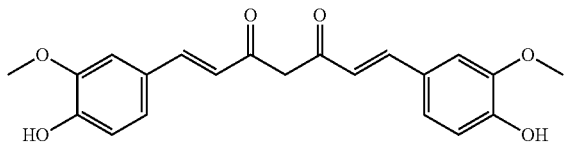

DMC is depicted below:

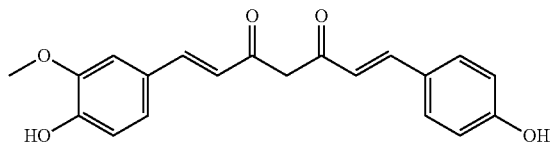 [SMILES: COc1cc(/C=C/C(=O)CC(=O)/C=C/c2ccc(O)cc2)ccc1O]

BDMC is depicted below:

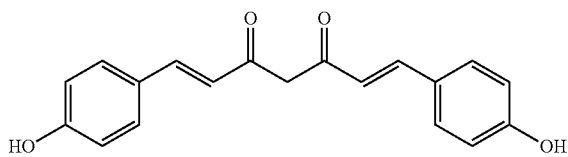 [SMILES: O=C(/C=C/c1ccc(O)cc1)CC(=O)/C=C/c1ccc(O)cc1]

Tetrahydrocurcumin is depicted below:

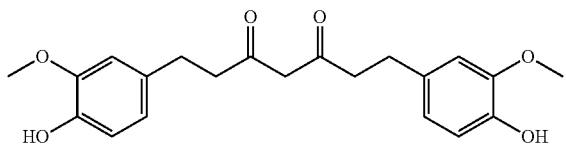

Dihydrocurcumin is depicted as follows:

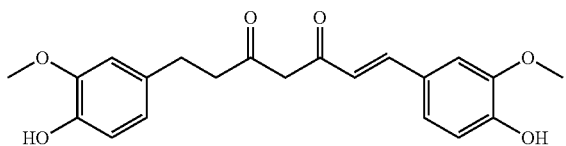

Hexahydrocurcumin is depicted as follows:

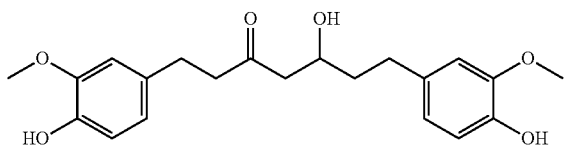

Octahydrocurcumin is depicted as follows:

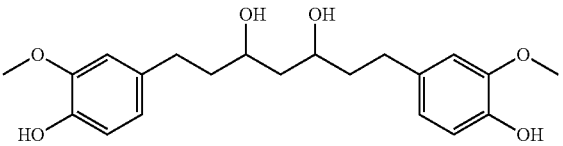

In some embodiments, a curcumin composition, as described herein, may comprise an amount of at least two of diferuloylmethane, DMC, BDMC, tetrahydrocurcumin, dihydrocurcumin, hexahydrocurcumin, and octahydrocurcumin. For example, a curcumin composition can comprise an amount of diferuloylmethane and an amount of DMC present in a ratio of about 1:1, or about 20:1 to about 1:20 of diferuloylmethane to DMC, or any range therebetween. In some embodiments, a curcumin composition can comprise an amount of diferuloylmethane and an amount of BDMC present in a ratio of about 1:1, or about 20:1 to about 1:20 of diferuloylmethane to BDMC, or any range therebetween. In certain embodiments, a curcumin composition can comprise an amount of diferuloylmethane and an amount of tetrahydrocurcumin present in a ratio of about 1:1, or about 20:1 to about 1:20 of diferuloylmethane to tetrahydrocurcumin, or any range therebetween. In some embodiments, a curcumin composition can comprise an amount of diferuloylmethane and an amount of dihydrocurcumin present in a ratio of about 1:1, or about 20:1 to about 1:20 of diferuloylmethane to dihydrocurcumin, or any range therebetween. In certain embodiments, a curcumin composition can comprise an amount of diferuloylmethane and an amount of hexahydrocurcumin present in a ratio of about 1:1, or about 20:1 to about 1:20 of diferuloylmethane to hexahydrocurcumin, or any range therebetween. In some embodiments, a curcumin composition can comprise an amount of diferuloylmethane and an amount of octahydrocurcumin present in a ratio of about 1:1, or about 20:1 to about 1:20 of diferuloylmethane to octahydrocurcumin, or any range therebetween. In certain embodiments, a curcumin composition can comprise an amount of DMC and an amount of BDMC present in a ratio of about 1:1, or about 20:1 to about 1:20 of DMC to BDMC, or any range therebetween. In some embodiments, a curcumin composition can comprise an amount of DMC and an amount of tetrahydrocurcumin present in a ratio of about 1:1, or about 20:1 to about 1:20 of DMC to tetrahydrocurcumin, or any range therebetween. In certain embodiments, a curcumin composition can comprise an amount of DMC and an amount of dihydrocurcumin present in a ratio of about 1:1, or about 20:1 to about 1:20 of DMC to dihydrocurcumin, or any range therebetween. In some embodiments, a curcumin composition can comprise an amount of DMC and an amount of hexahydrocurcumin present in a ratio of about 1:1, or about 20:1 to about 1:20 of DMC to hexahydrocurcumin, or any range therebetween. In certain embodiments, a curcumin composition can comprise an amount of DMC and an amount of octahydrocurcumin present in a ratio of about 1:1, or about 20:1 to about 1:20 of DMC to octahydrocurcumin, or any range therebetween. In some embodiments, a curcumin composition can comprise an amount of BDMC and an amount of tetrahydrocurcumin present in a ratio of about 1:1, or about 20:1 to about 1:20 of BDMC to tetrahydrocurcumin, or any range therebetween. In certain embodiments, a curcumin composition can comprise an amount of BDMC and an amount of dihydrocurcumin present in a ratio of about 1:1, or about 20:1 to about 1:20 of BDMC to dihydrocurcumin, or any range therebetween. In some embodiments, a curcumin composition can comprise an amount of BDMC and an amount of hexahydrocurcumin present in a ratio of about 1:1, or about 20:1 to about 1:20 of BDMC to hexahydrocurcumin, or any range therebetween. In certain embodiments, a curcumin composition can comprise an amount of BDMC and an amount of octahydrocurcumin present in a ratio of about 1:1, or about 20:1 to about 1:20 of BDMC to octahydrocurcumin, or any range therebetween. In certain embodiments, a curcumin composition can comprise an amount of tetrahydrocurcumin and an amount of dihydrocurcumin present in a ratio of about 1:1, or about 20:1 to about 1:20 of tetrahydrocurcumin to dihydrocurcumin, or any range therebetween. In some embodiments, a curcumin composition can comprise an amount of tetrahydrocurcumin and an amount of hexahydrocurcumin present in a ratio of about 1:1, or about 20:1 to about 1:20 of tetrahydrocurcumin to hexahydrocurcumin, or any range therebetween. In certain embodiments, a curcumin composition can comprise an amount of tetrahydrocurcumin and an amount of octahydrocurcumin present in a ratio of about 1:1, or about 20:1 to about 1:20 of tetrahydrocurcumin to octahydrocurcumin, or any range therebetween. In some embodiments, a curcumin composition can comprise an amount of dihydrocurcumin and an amount of hexahydrocurcumin present in a ratio of about 1:1, or about 20:1 to about 1:20 of dihydrocurcumin to hexahydrocurcumin, or any range therebetween. In certain embodiments, a curcumin composition can comprise an amount of dihydrocurcumin and an amount of octahydrocurcumin present in a ratio of about 1:1, or about 20:1 to about 1:20 of dihydrocurcumin to octahydrocurcumin, or any range therebetween. In certain embodiments, a curcumin composition can comprise an amount of hexahydrocurcumin and an amount of octahydrocurcumin present in a ratio of about 1:1, or about 20:1 to about 1:20 of hexahydrocurcumin to octahydrocurcumin, or any range therebetween. As described further herein, any two of the aforementioned compounds can be present in a ratio of about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, or any ratio in between. In view of the results and discussion contained herein, one of skill in the art would understand how to formulate a curcumin composition of the instant disclosure to achieve the results described herein.

In certain embodiments, a curcumin composition, as described herein, may comprise an amount of three or more of diferuloylmethane, DMC, BDMC, tetrahydrocurcumin, dihydrocurcumin, hexahydrocurcumin, and octahydrocurcumin. The three or more compounds may be present in a ratio. The ratio can be understood as comprising a "part" of any compound. For example, a curcumin composition may comprise a ratio of 4:1:10, diferuloylmethane to DMC to BDMC, corresponding to 4 parts diferuloylmethane, 1 part DMC, and 10 parts BDMC. The individual amount of any of the aforementioned compounds may be as low as 1 part, may be as high as 20 parts, or may any value therebetween. In view of the results and discussion contained herein, one of skill in the art would understand how to formulate a curcumin composition of the instant disclosure to achieve the results described herein.

Some embodiments provide a composition comprising an amount of one or more green tea extracts formulated as a green tea extract composition. In certain embodiments, a green tea extract composition can comprise an amount of epigallocatechin gallate (EGCG), an amount of epicatechin (EC), an amount of epigallocatechin (EGC), an amount of epicatechin gallate (ECG), or a combination of any of the foregoing. In some embodiments, a green tea extract composition, as described herein, may comprise a pharmaceutically acceptable vehicle, carrier, or diluent.

EGCG is depicted below:

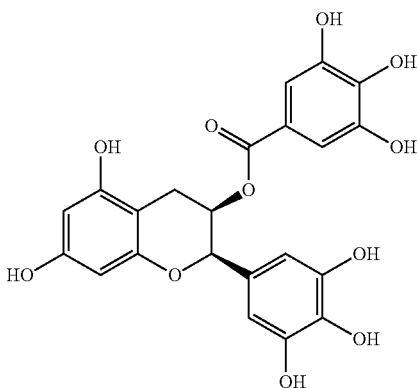 [SMILES: O=C(O[C@@H]1Cc2c(O)cc(O)cc2O[C@@H]1c1cc(O)c(O)c(O)c1)c1cc(O)c(O)c(O)c1]

EC is depicted below:

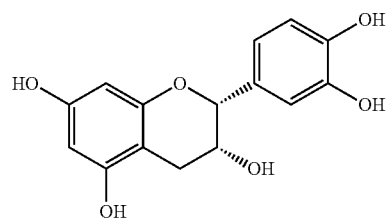 [SMILES: Oc1cc(O)c2c(c1)O[C@H](c1ccc(O)c(O)c1)[C@H](O)C2]

EGC is depicted below:

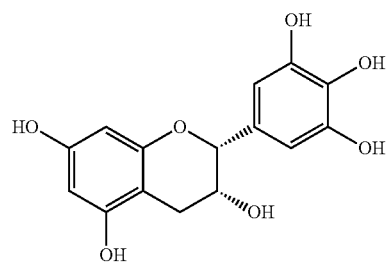 [SMILES: Oc1cc(O)c2c(c1)O[C@H](c1cc(O)c(O)c(O)c1)[C@H](O)C2]

ECG is depicted below:

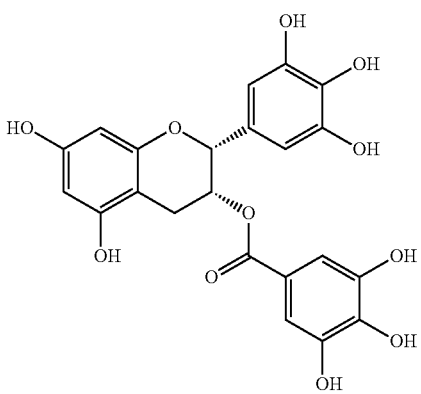 [SMILES: O=C(O[C@@H]1Cc2c(O)cc(O)cc2O[C@@H]1c1cc(O)c(O)c(O)c1)c1cc(O)c(O)c(O)c1]

In some embodiments, a green tea extract composition, as described herein, may comprise an amount of at least two of EGCG, EC, EGC, and ECG. For example, a green tea extract composition can comprise an amount of EGCG and an amount of EC present in a ratio of about 1:1, or about 20:1 to about 1:20 of EGCG to EC, or any range therebetween. In some embodiments, a green tea extract composition can comprise an amount of EGCG and an amount of EGC present in a ratio of about 1:1, or about 20:1 to about 1:20 of EGCG to EGC, or any range therebetween. In certain embodiments, a green tea extract composition can comprise an amount of EGCG and an amount of ECG present in a ratio of about 1:1, or about 20:1 to about 1:20 of EGCG to ECG, or any range therebetween. In some embodiments, a green tea extract composition can comprise an amount of EC and an amount of EGC present in a ratio of about 1:1, or about 20:1 to about 1:20 of EC to EGC, or any range therebetween. In certain embodiments, a green tea extract composition can comprise an amount of EC and an amount of ECG present in a ratio of about 1:1, or about 20:1 to about 1:20 of EC to ECG, or any range therebetween. In some embodiments, a green tea extract composition can comprise an amount of EGC and an amount of ECG present in a ratio of about 1:1, or about 20:1 to about 1:20 of EGC to ECG, or any range therebetween. As described further herein, any two of the aforementioned compounds can be present in a ratio of about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, or any ratio in between. In view of the results and discussion contained herein, one of skill in the art would understand how to formulate a green tea extract composition of the instant disclosure to achieve the results described herein.

In certain embodiments, a green tea extract composition, as described herein, may comprise an amount of three or more of EGCG, EC, EGC, and ECG. The three or more compounds may be present in a ratio. The ratio can be understood as comprising a "part" of any compound. For example, a green tea extract composition may comprise a ratio of 4:1:10, EGCG to EC to EGC, corresponding to 4 parts EGCG, 1 part EC, and 10 parts EGC. The individual amount of any of the aforementioned compounds may be as low as 1 part, may be as high as 20 parts, or may any value therebetween. In view of the results and discussion contained herein, one of skill in the art would understand how to formulate a green tea extract composition of the instant disclosure to achieve the results described herein.

Some embodiments provide a composition comprising an amount of one or more phycocyanin-related compounds formulated as a phycocyanin composition. As used herein, the term "phycocyanin-related compounds" refers to compounds that are pigment-proteins found in Spirulina, or compounds derived therefrom either by extraction, enzymatic degradation, or other known methods in the art. Exemplary examples of phycocyanin-related compounds include, but are not limited to phycocyanin, extracts of phycocyanin, phycocyanin peptides, and phycocyanin oligopeptides, and the like. In certain embodiments, a phycocyanin composition can comprise an amount of phycocyanin, an amount of an extract of phycocyanin, an amount of phycocyanin peptides, an amount of phycocyanin oligopeptides, or a combination of any of the foregoing. In some embodiments, a phycocyanin composition, as described herein, may comprise a pharmaceutically acceptable vehicle, carrier, or diluent.

In some embodiments, a phycocyanin composition, as described herein, may comprise an amount of at least two of phycocyanin or an extract thereof, phycocyanin peptides, or phycocyanin oligopeptides. For example, a phycocyanin composition can comprise an amount of phycocyanin and an amount of an extract of phycocyanin present in a ratio of about 1:1, or about 20:1 to about 1:20 of phycocyanin to an extract of phycocyanin, or any range therebetween. In some embodiments, a phycocyanin composition can comprise an amount of phycocyanin and an amount of phycocyanin peptides present in a ratio of about 1:1, or about 20:1 to about 1:20 of phycocyanin to phycocyanin peptides, or any range therebetween. In certain embodiments, a green tea extract composition can comprise an amount of phycocyanin and an amount of phycocyanin oligopeptides present in a ratio of about 1:1, or about 20:1 to about 1:20 of phycocyanin to phycocyanin oligopeptides, or any range therebetween. In some embodiments, a phycocyanin composition can comprise an amount of an extract of phycocyanin and an amount of phycocyanin peptides present in a ratio of about 1:1, or about 20:1 to about 1:20 of an extract of phycocyanin to phycocyanin peptides, or any range therebetween. In certain embodiments, a green tea extract composition can comprise an amount of an extract of phycocyanin and an amount of phycocyanin oligopeptides present in a ratio of about 1:1, or about 20:1 to about 1:20 of an extract of phycocyanin to phycocyanin oligopeptides, or any range therebetween. In some embodiments, a green tea extract composition can comprise an amount of phycocyanin peptides and an amount of phycocyanin oligopeptides present in a ratio of about 1:1, or about 20:1 to about 1:20 of phycocyanin peptides to phycocyanin oligopeptides, or any range therebetween. As described further herein, any two of the aforementioned compounds can be present in a ratio of about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, or any ratio in between. In view of the results and discussion contained herein, one of skill in the art would understand how to formulate a phycocyanin composition of the instant disclosure to achieve the results described herein.

In certain embodiments, a phycocyanin composition, as described herein, may comprise an amount of three or more of phycocyanin, an extract of phycocyanin, phycocyanin peptides, and phycocyanin oligopeptides. The three or more compounds may be present in a ratio. The ratio can be understood as comprising a "part" of any compound. For example, a phycocyanin composition may comprise a ratio of 4:1:10, phycocyanin to phycocyanin peptides to phycocyanin oligopeptides, corresponding to 4 parts phycocyanin, 1 part phycocyanin peptides, and 10 parts phycocyanin oligopeptides. The individual amount of any of the aforementioned compounds may be as low as 1 part, may be as high as 20 parts, or may any value therebetween. In view of the results and discussion contained herein, one of skill in the art would understand how to formulate a phycocyanin composition of the instant disclosure to achieve the results described herein.

Some embodiments provide a composition comprising an amount of a curcumin composition, as described herein, an amount of a green tea extract composition, as described herein, an amount of a phycocyanin composition, as described herein, or any combination of the foregoing formulated as a combination composition.

In some embodiments, a combination composition, as described herein, may comprise an amount of at least two of a curcumin composition, as described herein, a green tea extract composition, as described herein, and a phycocyanin composition, as described herein. For example, a combination composition can comprise an amount of a curcumin composition, as described herein, and an amount of a green tea extract composition, as described herein, present in a ratio of about 1:1, or about 20:1 to about 1:20 of a curcumin composition, as described herein, to a green tea extract composition, as described herein, or any range therebetween. In some embodiments, a combination composition can comprise an amount of a curcumin composition, as described herein, and an amount of a phycocyanin composition, as described herein, present in a ratio of about 1:1, or about 20:1 to about 1:20 of a curcumin composition, as described herein, to a phycocyanin composition, as described herein, or any range therebetween. In certain embodiments, a combination composition can comprise an amount of a green tea extract composition, as described herein, and an amount of a phycocyanin composition, as described herein, present in a ratio of about 1:1, or about 20:1 to about 1:20 of a green tea extract composition, as described herein, to a phycocyanin composition, as described herein, or any range therebetween. As described further herein, any two of the aforementioned compositions comprising a combination composition can be present in a ratio of about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, or any ratio in between. In view of the results and discussion contained herein, one of skill in the art would understand how to formulate a combination composition of the instant disclosure to achieve the results described herein.

In certain embodiments, a combination composition, as described herein, may comprise an amount of a curcumin composition, as described herein, an amount of a green tea extract composition, as described herein, and an amount of a phycocyanin composition, as described herein, provided as a ratio. The ratio of curcumin composition to green tea extract composition to phycocyanin may be provided in a ratio of about 1:1:1, 1:1:2, 1:1:3, 1:1:4, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1, 2:1:2, 2:1:3, 2:1:4, 2:1:5, 2:1:6, 2:1:7, 2:1:8, 2:1:9, 2:1:10, 2:2:1, 2:2:2, 2:2:3, 2:2:4, 2:2:5, 2:2:6, 2:2:7, 2:2:8, 2:2:9, 2:2:10, 2:3:1, 2:3:2, 2:3:3, 2:3:4, 2:3:5, 2:3:6, 2:3:7, 2:3:8, 2:3:9, 2:3:10, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1, 3:1:2, 3:1:3, 3:1:4, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1, 4:1:2, 4:1:3, 4:1:4, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1, 5:1:2, 5:1:3, 5:1:4, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, 10:10:10, or any ratio in between. In view of the results and discussion contained herein, one of skill in the art would understand how to formulate a combination composition comprising a curcumin composition, as described herein, a green tea extract, as described herein, and a phycocyanin composition, as described here, to achieve the results described herein.

In certain embodiments, a combination composition can comprise about 4.5:4.5:1 of diferuloylmethane to EGCG to phycocyanin or an extract thereof, about 6:3:1 of diferuloylmethane to EGCG to phycocyanin or an extract thereof, about 7.2:1.8:1 of diferuloylmethane to EGCG to phycocyanin or an extract thereof, or any ratio between about 8:1:1 to about 1:8:1 of diferuloylmethane to EGCG to phycocyanin or an extract thereof.

In certain embodiments, a combination composition can comprise about 4.5:4.5:1 of diferuloylmethane to EC to phycocyanin or an extract thereof, about 6:3:1 of diferuloylmethane to EC to phycocyanin or an extract thereof, about 7.2:1.8:1 of diferuloylmethane to EC to phycocyanin or an extract thereof, or any ratio between about 8:1:1 to about 1:8:1 of diferuloylmethane to EC to phycocyanin or an extract thereof.

In certain embodiments, a combination composition can comprise about 4.5:4.5:1 of diferuloylmethane to EGC to phycocyanin or an extract thereof, about 6:3:1 of diferuloylmethane to EGC to phycocyanin or an extract thereof, about 7.2:1.8:1 of diferuloylmethane to EGC to phycocyanin or an extract thereof, or any ratio between about 8:1:1 to about 1:8:1 of diferuloylmethane to EGC to phycocyanin or an extract thereof.

In certain embodiments, a combination composition can comprise about 4.5:4.5:1 of diferuloylmethane to ECG to phycocyanin or an extract thereof, about 6:3:1 of diferuloylmethane to ECG phycocyanin or an extract thereof, about 7.2:1.8:1 of diferuloylmethane to ECG to phycocyanin or an extract thereof, or any ratio between about 8:1:1 to about 1:8:1 of diferuloylmethane to ECG to phycocyanin or an extract thereof.

In certain embodiments, a combination composition can comprise about 4.5:4.5:1 of DMC to EGCG to phycocyanin or an extract thereof, about 6:3:1 of DMC to EGCG to phycocyanin or an extract thereof, about 7.2:1.8:1 of DMC to EGCG to phycocyanin or an extract thereof, or any ratio between about 8:1:1 to about 1:8:1 of DMC to EGCG to phycocyanin or an extract thereof.

In certain embodiments, a combination composition can comprise about 4.5:4.5:1 of DMC to EC to phycocyanin or an extract thereof, about 6:3:1 of DMC to EC to phycocyanin or an extract thereof, about 7.2:1.8:1 of DMC to EC to phycocyanin or an extract thereof, or any ratio between about 8:1:1 to about 1:8:1 of DMC to EC to phycocyanin or an extract thereof.

In certain embodiments, a combination composition can comprise about 4.5:4.5:1 of DMC to EGC to phycocyanin or an extract thereof, about 6:3:1 of DMC to EGC to phycocyanin or an extract thereof, about 7.2:1.8:1 of DMC to EGC to phycocyanin or an extract thereof, or any ratio between about 8:1:1 to about 1:8:1 of DMC to EGC to phycocyanin or an extract thereof.

In certain embodiments, a combination composition can comprise about 4.5:4.5:1 of DMC to ECG to phycocyanin or an extract thereof, about 6:3:1 of DMC to ECG to phycocyanin or an extract thereof, about 7.2:1.8:1 of DMC to ECG to phycocyanin or an extract thereof, or any ratio between about 8:1:1 to about 1:8:1 of DMC to ECG to phycocyanin or an extract thereof.

In certain embodiments, a combination composition can comprise about 4.5:4.5:1 of BDMC to EGCG to phycocyanin or an extract thereof, about 6:3:1 of BDMC to EGCG to phycocyanin or an extract thereof, about 7.2:1.8:1 of BDMC to EGCG to phycocyanin or an extract thereof, or any ratio between about 8:1:1 to about 1:8:1 of BDMC to EGCG to phycocyanin or an extract thereof.

In certain embodiments, a combination composition can comprise about 4.5:4.5:1 of BDMC to EC to phycocyanin or an extract thereof, about 6:3:1 of BDMC to EC to phycocyanin or an extract thereof, about 7.2:1.8:1 of BDMC to EC to phycocyanin or an extract thereof, or any ratio between about 8:1:1to about 1:8:1 of BDMC to EC to phycocyanin or an extract thereof.

In certain embodiments, a combination composition can comprise about 4.5:4.5:1 of BDMC to EGC to phycocyanin or an extract thereof, about 6:3:1 of BDMC to EGC to phycocyanin or an extract thereof, about 7.2:1.8:1 of BDMC to EGC to phycocyanin or an extract thereof, or any ratio between about 8:1:1 to about 1:8:1 of BDMC to EGC to phycocyanin or an extract thereof.

In certain embodiments, a combination composition can comprise about 4.5:4.5:1 of BDMC to ECG to phycocyanin or an extract thereof, about 6:3:1 of BDMC to ECG to phycocyanin or an extract thereof, about 7.2:1.8:1 of BDMC to ECG to phycocyanin or an extract thereof, or any ratio between about 8:1:1 to about 1:8:1 of BDMC to ECG to phycocyanin or an extract thereof.

In certain embodiments, a combination composition can comprise about 4.5:4.5:1 of tetrahydrocurcumin to EGCG to phycocyanin or an extract thereof, about 6:3:1 of tetrahydrocurcumin to EGCG to phycocyanin or an extract thereof, about 7.2:1.8:1 of tetrahydrocurcumin to EGCG to phycocyanin or an extract thereof, or any ratio between about 8:1:1 to about 1:8:1 of tetrahydrocurcumin to EGCG to phycocyanin or an extract thereof.

In certain embodiments, a combination composition can comprise about 4.5:4.5:1 of tetrahydrocurcumin to EC to phycocyanin or an extract thereof, about 6:3:1 of tetrahydrocurcumin to EC to phycocyanin or an extract thereof, about 7.2:1.8:1 of tetrahydrocurcumin to EC to phycocyanin or an extract thereof, or any ratio between about 8:1:1 to about 1:8:1 of tetrahydrocurcumin to EC to phycocyanin or an extract thereof.

In certain embodiments, a combination composition can comprise about 4.5:4.5:1 of tetrahydrocurcumin to EGC to phycocyanin or an extract thereof, about 6:3:1 of tetrahydrocurcumin to EGC to phycocyanin or an extract thereof, about 7.2:1.8:1 of tetrahydrocurcumin to EGC to phycocyanin or an extract thereof, or any ratio between about 8:1:1 to about 1:8:1 of tetrahydrocurcumin to EGC to phycocyanin or an extract thereof.

In certain embodiments, a combination composition can comprise about 4.5:4.5:1 of tetrahydrocurcumin to ECG to phycocyanin or an extract thereof, about 6:3:1 of tetrahydrocurcumin to ECG to phycocyanin or an extract thereof, about 7.2:1.8:1 of tetrahydrocurcumin to ECG to phycocyanin or an extract thereof, or any ratio between about 8:1:1 to about 1:8:1 of tetrahydrocurcumin to ECG to phycocyanin or an extract thereof.

In certain embodiments, a combination composition can comprise about 4.5:4.5:1 of dihydrocurcumin to EGCG to phycocyanin or an extract thereof, about 6:3:1 of dihydrocurcumin to EGCG to phycocyanin or an extract thereof, about 7.2:1.8:1 of dihydrocurcumin to EGCG to phycocyanin or an extract thereof, or any ratio between about 8:1:1 to about 1:8:1 of dihydrocurcumin to EGCG to phycocyanin or an extract thereof.

In certain embodiments, a combination composition can comprise about 4.5:4.5:1 of dihydrocurcumin to EC to phycocyanin or an extract thereof, about 6:3:1 of dihydrocurcumin to EC to phycocyanin or an extract thereof, about 7.2:1.8:1 of dihydrocurcumin to EC to phycocyanin or an extract thereof, or any ratio between about 8:1:1 to about 1:8:1 of dihydrocurcumin to EC to phycocyanin or an extract thereof.

In certain embodiments, a combination composition can comprise about 4.5:4.5:1 of dihydrocurcumin to EGC to phycocyanin or an extract thereof, about 6:3:1 of dihydrocurcumin to EGC to phycocyanin or an extract thereof, about 7.2:1.8:1 of dihydrocurcumin to EGC to phycocyanin or an extract thereof, or any ratio between about 8:1:1 to about 1:8:1 of dihydrocurcumin to EGC to phycocyanin or an extract thereof.

In certain embodiments, a combination composition can comprise about 4.5:4.5:1 of dihydrocurcumin to ECG to phycocyanin or an extract thereof, about 6:3:1 of dihydrocurcumin to ECG to phycocyanin or an extract thereof, about 7.2:1.8:1 of dihydrocurcumin to ECG to phycocyanin or an extract thereof, or any ratio between about 8:1:1 to about 1:8:1 of dihydrocurcumin to ECG to phycocyanin or an extract thereof.

In certain embodiments, a combination composition can comprise about 4.5:4.5:1 of hexahydrocurcumin to EGCG to phycocyanin or an extract thereof, about 6:3:1 of hexahydrocurcumin to EGCG to phycocyanin or an extract thereof, about 7.2:1.8:1 of hexahydrocurcumin to EGCG to phycocyanin or an extract thereof, or any ratio between about 8:1:1 to about 1:8:1 of hexahydrocurcumin to EGCG to phycocyanin or an extract thereof.

In certain embodiments, a combination composition can comprise about 4.5:4.5:1 of hexahydrocurcumin to EC to phycocyanin or an extract thereof, about 6:3:1 of hexahydrocurcumin to EC to phycocyanin or an extract thereof, about 7.2:1.8:1 of hexahydrocurcumin to EC to phycocyanin or an extract thereof, or any ratio between about 8:1:1 to about 1:8:1 of hexahydrocurcumin to EC to phycocyanin or an extract thereof.

In certain embodiments, a combination composition can comprise about 4.5:4.5:1 of hexahydrocurcumin to EGC to phycocyanin or an extract thereof, about 6:3:1 of hexahydrocurcumin to EGC to phycocyanin or an extract thereof, about 7.2:1.8:1 of hexahydrocurcumin to EGC to phycocyanin or an extract thereof, or any ratio between about 8:1:1 to about 1:8:1 of hexahydrocurcumin to EGC to phycocyanin or an extract thereof.

In certain embodiments, a combination composition can comprise about 4.5:4.5:1 of hexahydrocurcumin to ECG to phycocyanin or an extract thereof, about 6:3:1 of hexahydrocurcumin to ECG to phycocyanin or an extract thereof, about 7.2:1.8:1 of hexahydrocurcumin to ECG to phycocyanin or an extract thereof, or any ratio between about 8:1:1 to about 1:8:1 of hexahydrocurcumin to ECG to phycocyanin or an extract thereof.

In certain embodiments, a combination composition can comprise about 4.5:4.5:1 of octahydrocurcumin to EGCG to phycocyanin or an extract thereof, about 6:3:1 of octahydrocurcumin to EGCG to phycocyanin or an extract thereof, about 7.2:1.8:1 of octahydrocurcumin to EGCG to phycocyanin or an extract thereof, or any ratio between about 8:1:1 to about 1:8:1 of octahydrocurcumin to EGCG to phycocyanin or an extract thereof.

In certain embodiments, a combination composition can comprise about 4.5:4.5:1 of octahydrocurcumin to EC to phycocyanin or an extract thereof, about 6:3:1 of octahydrocurcumin to EC to phycocyanin or an extract thereof, about 7.2:1.8:1 of octahydrocurcumin to EC to phycocyanin or an extract thereof, or any ratio between about 8:1:1 to about 1:8:1 of octahydrocurcumin to EC to phycocyanin or an extract thereof.

In certain embodiments, a combination composition can comprise about 4.5:4.5:1 of octahydrocurcumin to EGC to phycocyanin or an extract thereof, about 6:3:1 of octahydrocurcumin to EGC to phycocyanin or an extract thereof, about 7.2:1.8:1 of octahydrocurcumin to EGC to phycocyanin or an extract thereof, or any ratio between about 8:1:1 to about 1:8:1 of octahydrocurcumin to EGC to phycocyanin or an extract thereof.

In certain embodiments, a combination composition can comprise about 4.5:4.5:1 of octahydrocurcumin to ECG to phycocyanin or an extract thereof, about 6:3:1 of octahydrocurcumin to ECG to phycocyanin or an extract thereof, about 7.2:1.8:1 of octahydrocurcumin to ECG to phycocyanin or an extract thereof, or any ratio between about 8:1:1 to about 1:8:1 of octahydrocurcumin to ECG to phycocyanin or an extract thereof.

In some embodiments, a combination composition, as described herein, may comprise between about 10 μg to about 10 g of one or more of a curcumin composition, as described herein, a green tea extract composition, as described herein, and a phycocyanin composition, as described herein. For example, some embodiments include a combination composition comprising one or more of a of a curcumin composition, as described herein, a green tea extract composition, as described herein, and a phycocyanin composition, as described herein present at an amount of about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, a curcumin composition, a green tea extract composition, a phycocyanin composition, or a combination composition, as described herein, can comprise one or more supplement ingredients. As used herein, the term supplement ingredient can refer to essential fatty acids such as linolenic acid and linoleic acid, and essential amino acids such as tryptophan, lysine, methionine, phenylalanine, threonine, valine, leucine, isoleucine, arginine, and histidine, and n-acetyl cysteine. Also included within the meaning of supplement ingredients are vitamins such as retinol (vitamin A), thiamine (vitamin B1), riboflavin (vitamin B2), niacin (vitamin B3), pantothenic acid (vitamin B5), pyridoxine, pyridoxamine, or pyridoxal (vitamin B6), biotin (vitamin B7) or pharmaceutically acceptable salts thereof, folic acid (vitamin B9) or pharmaceutically acceptable salts thereof, cobalamin (vitamin B12), choline, ascorbic acid (vitamin C) or pharmaceutically acceptable salts thereof, ergocalciferol (vitamin D2), calciferol (vitamin D3), 22-dihydroergocalciferol (vitamin D4), sitocalciferol (vitamin D5), tocopherol (vitamin E), phylloquinone (vitamin K1), menaquinone (vitamin K2), menadione (vitamin K3), or any combination of the foregoing. Other vitamins not explicitly listed would readily be envisaged by those of skill in the art, in view of the disclosure contained herein. Supplement ingredients can further include dietary minerals such as, for example, chromium, bromine, cobalt, copper, fluorine, germanium, iodine, iron, magnesium, manganese, molybdenum, potassium, selenium, silicon, zinc, calcium, phosphorous, sodium, sulfur, and vanadium. Supplement ingredients can also comprise cranberry extract, turmeric, royal jelly, açaí berry, beet root, coral calcium, oyster shell, gotu kola, Gingko biloba, lions mane mushroom, pomegranate, hibiscus flower, strawberry powder, dandelion root, celery powder, parsley powder, peppermint leaf, cinnamon bark powder, maca root, nicotinamide riboside, resveratrol, NAD+ precursors, Coenzyme Q10, omega-3-fatty acids, cabbage powder, pterostilbene, nicotinamide mononucleotide, and combinations thereof. Supplement ingredients can include nitrates such as citrulline nitrate, creatine nitrate, beta-alanine nitrate, and the like. Compositions described herein can include one or more of the foregoing supplement ingredients, as would be understood by one of skill in the art.

In some embodiments, an amount of least one supplemental ingredient, as disclosed herein, can be about 10 µg to about 10 g. For example, the amount of the at least one supplemental ingredient in the composition can be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In certain embodiments, a curcumin composition, a green tea extract composition, a phycocyanin composition, or a combination composition, as described herein, can be formulated as a dietary supplement or pharmaceutical agent.

The compounds comprising curcumin compositions, green tea extract compositions, and phycocyanin compositions, as described herein, may be an active agent present in a therapeutically effective amount. By way of example, a "therapeutically effective amount" and/or an "effective amount" of the compound disclosed herein can be (on a dosage weight per subject weight basis), for example, 0.1 µg/kg, 0.5 µg/kg, 1 µg/kg, 1.5 µg/kg, 2.0 µg/kg, 2.5 µg/kg, 3.0 µg/kg, 3.5 µg/kg, 4.0 µg/kg, 4.5 µg/kg, 5.0 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 80 µg/kg 0, 850 µg/kg, 900 µg/kg, 1 mg/kg, 1.5 mg/kg, 2.0 mg/kg, 2.5 mg/kg, 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, or more, or any fraction or integer in between any two of the preceding amounts of the compound. An effective amount may include any of the ranges and amounts discussed herein.

Accordingly, in some embodiments, the dose of the compound in compositions disclosed herein (corresponding to the therapeutically effective amount), can be about 10 µg to about 10 g, preferably per day. For example, the amount of the composition can be 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any range or amount in between any two of the preceding values and any other ranges or amounts disclosed herein.

In some embodiments, a curcumin composition, as described herein, a green tea extract composition, as described herein, and a phycocyanin composition, as described herein, are provided in a synergistic ratio in a combination composition, and optionally, the combination composition may be provided as a dietary supplement or pharmaceutical agent. The synergistic ratio is not particularly limited. In some embodiments the synergistic ratio can comprise 4.5:4.5:1 of curcumin composition to green tea extract composition to phycocyanin composition. In some embodiments the synergistic ratio can comprise 6:3:1 of curcumin composition to green tea extract composition to phycocyanin composition. In some embodiments the synergistic ratio can comprise 7.2:1.8:1 of curcumin composition to green tea extract composition to phycocyanin composition. In some embodiments the synergistic can comprise any ratio between about 8:1:1 to about 1:8:1 of curcumin composition to green tea extract composition phycocyanin composition.

In some embodiments, compositions, as described herein, can be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

In some embodiments, a ramping administration protocol where a subject is administered temporally increasing amounts of compositions described herein can be utilized. For example, a subject could be administered with 100 mg of a composition as described herein per day for 7 days, followed by 200 mg, for the next 7 days, followed by 300 mg for the next 7 days. Administration protocols can also follow a pattern whereby the dosage amount decreases over time. For example, 300 mg of a composition as described herein per day for 7 days, followed by 200 mg, for the next 7 days, followed by 100 mg for the next 7 days. In some embodiments, the methods as described herein can be utilized in combination with a calorie restriction protocol in a subject. In certain embodiments, the compositions described herein may be administered before, after, or during a meal. In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and may be administered to the patient at any time from diagnosis onwards. The composition may be administered as the sole treatment or in conjunction with other drugs or therapies useful in treating the condition in question.

The present disclosure discloses combination compositions comprising one or more of a curcumin composition, a green tea extract composition, and a phycocyanin composition, optionally formulated as a nutritional supplement or pharmaceutical agent, useful as an NK3 antagonist, and methods of using the same. Some embodiments provide solid dosage forms of the compositions disclosed herein. Certain embodiments provide aqueous solutions of compositions disclosed herein. Embodiments described herein comprising compositions disclosed herein as a nutritional supplement means that the composition disclosed herein is present in an unnatural form, i.e., is presented in a supplement (e.g., in a pill or powder) that is different from that which occurs naturally, or the nutritional or dietary supplement results in unnatural supplementation that is unachievable through a non-supplemented diet. Some embodiments can further comprise a matrix material such as a fatty acid, fatty acid ester, triglycerides, oils, lipid solvents, and the like. In some embodiments, a composition is a solid composition. In some embodiments, the composition comprises a sustained-release matrix. In some embodiments, the composition is enteric coated.

Some embodiments provide physiologically compatible compositions, as disclosed herein, including hydrates, crystalline forms, polymorphic forms, solid forms having specific bulk densities or tap densities, and solid forms having specific particle sizes. Some embodiments provide compositions coated with pharmaceutically acceptable materials intended to modify its release and/or bioavailability, including, but not limited to Eudragit®, microcrystalline cellulose, hydroxypropylmethylcellulose phthalate, and the like.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin, or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin, or olive oil. Aqueous suspensions can contain the complex of the described herein admixed with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water can provide the active ingredient in admixture with a dispersing or wetting agent, a suspending agent, and one or more preservatives. Additional excipients, for example sweetening, flavoring, and coloring agents, can also be present.

Syrups and elixirs can be formulated with sweetening agents, such as glycerol, sorbitol, or sucrose. Such formulations can also contain a demulcent, a preservative, a flavoring, or a coloring agent.

The composition for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution, and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

It will be appreciated that the amount of the compound may be combined with a carrier material to produce a single dosage form. Such forms will vary depending upon the host treated and the particular mode of administration.

In some aspects, compositions described herein may be administered via supplements or dosages designed for animals. In some animal applications, the compound or composition may be added to and/or comprise a pet treat or biscuit, for example, a dog biscuit or a cat treat.

Aqueous suspensions may contain the compound disclosed herein in admixture with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Utilization of controlled release vehicles would readily be envisaged by those of skill in the pharmaceutical sciences in view of the disclosure contained herein, and these aspects can be applied to nutritional and dietary supplements. The technology and products in this art are variably referred to as controlled release, sustained release, prolonged action, depot, repository, delayed action, retarded release, and timed release; the words "controlled release" as used herein is intended to incorporate each of the foregoing technologies.

Numerous controlled release vehicles can be used, including biodegradable or bioerodible polymers such as polylactic acid, polyglycolic acid, and regenerated collagen. Controlled release drug delivery devices can include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, and can be used in the disclosed methods.

Controlled release preparations can be achieved by the use of polymers to form complexes with or absorb a curcumin composition. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein a composition as disclosed herein is dissolved in an aqueous constituent to gradually release over time, can be prepared by copolymerization of hydrophilic mono-olefinic monomers such as ethylene glycol methacrylate. Matrix devices, wherein a curcumin composition is dispersed in a matrix of carrier material, can be used. The carrier can be porous, non-porous, solid, semi-solid, permeable, or impermeable. Alternatively, a device comprising a central reservoir of a composition disclosed herein surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations can also be used. In an embodiment, a composition as described herein is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

In some embodiments, dosing for oral administration may be with a regimen calling for single daily dose, or for a single dose every other day, or for a single dose within 72 hours of the first administered dose, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to as long as about 72 hours, depending upon the properties of each active agent such as potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. In one aspect, the embodiments described herein can achieve therapeutic and/or nutraceutical benefits not previously recognized or achievable, and thus, unexpectedly, and surprisingly achieve improved abilities for using the compositions. In some embodiments a composition is formulated for intravenous administration because a more concentrated solution can be produced. Whether the active agents of the therapy are administered by oral or intravenous route, separately or together, each such active agent will be contained in a suitable pharmaceutical formulation of pharmaceutically-acceptable excipients, diluents, or other formulations components.

In certain embodiments, a combination composition according to the disclosure contained herein is administered to a subject as an NK3 antagonist. In certain embodiments, a composition, as described herein, is administered to a subject to treat, ameliorate, prevent, or reduce the effects of polycystic ovary syndrome. In certain embodiments, a composition as described herein is administered to a subject to support and/or maintain healthy levels of NK3 antagonism. In certain embodiments, a composition, as described herein, is administered to a subject to treat, ameliorate, prevent, or reduce the effects of infertility in women, hirsutism, acne, obesity, chronic anovulation, metabolic syndrome, type II diabetes mellitus, and combinations thereof. In certain embodiments, a composition, as described herein, is administered to support and/or maintain healthy fertility in women. In some embodiments, a composition, as described herein, is administered in combination with metabolic modulators such as metformin. In certain embodiments, a composition, as described herein, is administered to a subject to treat, ameliorate, prevent, or reduce the effects of cardiovascular disease and/or hypertension. In certain embodiments, a composition, as described herein, is administered to a subject to support and/or maintain healthy stress levels. In certain embodiments a woman with a body mass index exceeding 15 kg/m$^2$ and identified to have polycystic ovary syndrome is administered a composition, as described herein, to treat, ameliorate, prevent, or reduce the effects of polycystic ovary syndrome. In some embodiments, a composition, as described herein, is administered in combination with luteinizing hormone (LH) is administered to a subject to treat, ameliorate, prevent, or reduce the effects of one or more of the ailments described herein. In some embodiments, a composition, as described herein, is administered to a subject to treat, ameliorate, prevent, or reduce the effects of hot flashes. In some embodiments, a composition, as described herein, is administered to a menopausal woman to maintain a healthy level of hot flashes, i.e., to reduce the number, frequency, and/or severity of hot flashes.

Without being bound by any particular theory, it is believed that the compositions and/or dietary supplements disclosed herein act as antagonists by targeting signaling pathways associated with menopause. It is believed that the symptoms associated with menopause are characterized by, and result from, increased secretion of LH and follicle-stimulating hormone (FSH) from the pituitary gland. The increase in LH and FSH secretion is believed to be mediated by increased secretion of gonadotropin hormone-releasing hormone (GnRH) and resulting from increased kisspeptin and NKB signaling. Accordingly, it is believed that by blocking and/or restricting the increased signaling of kisspeptin and NKB in their associated pathways, with antagonists, the increased secretion of GnRH can be reduced, and ultimately the secretion of LH and FSH. By reducing secretion of LH and FSH, it is believed that the symptoms associated with menopause can treated, prevented, ameliorated, and/or the effects associated therewith can be reduced.

In some embodiments, a composition as described herein is administered to a subject to treat, ameliorate, prevent, or reduce the effects of mental, psychotic, and/or neuropsychiatric disorders such as schizophrenia, cognitive decline during aging, dementia, depression, Alzheimer's, and the like. In some embodiments, a composition as described herein is administered to support and/or maintain healthy cognitive function. In certain embodiments, a composition as described herein is administered to a subject to treat, ameliorate, prevent, or reduce the effects of neuroinflammation. In some embodiments, a composition as described herein is administered in combination with an antipsychotic drug, including but not limited to, aripiprazole, clozapine, olanzapine, risperidone, ziprasidone, quetiapine, haloperidol, osanetant, and/or talnetant. In some embodiments, a composition as described herein is administered to a subject to treat, ameliorate, prevent, or reduce the effects of drug, nicotine, and/or alcohol addiction. In some embodiments, composition as described herein is administered to a subject to reduce drug-seeking behavior.

In some embodiments, a composition as described herein is administered to a subject to treat, ameliorate, prevent, or reduce the effects of disorders associated with inflammation. For example, and without limitation, this includes central nervous system disorders (e.g., anxiety, psychosis, movement and convulsive disorders, and Parkinson' s), respiratory and pulmonary inflammatory disorders, skin disorders and itch, gastrointestinal disorders, renal and bladder diseases, inflammatory bowel disease, eating disorders, and chronic pain. In certain embodiments, a curcumin composition is administered to treat hormonal variations.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, the terms "prophylactic treatment," "prevent," or "preventing," can refer to treating a subject who does not yet exhibit symptoms of a disease or condition, but who is susceptible to, or otherwise at risk of, a particular disease or condition, whereby the treatment reduces the likelihood that the patient will develop the disease or condition. A "disorder" is any condition that would benefit from treatment with the compositions described herein.

As used herein, the terms "treating", "treatment" and the like are used herein to generally refer to obtaining a desired pharmacological and physiological effect and can also refer to a nutritional or nutraceutical effect, the scopes, and meanings of which will be clear to the skilled artisan based upon the context in which these terms are used. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms, conditions, and co-morbidities. The terms "optimum" or "healthy" and the like may be used to refer to the physiological amounts of NK3 activity in a mammal, wherein administration of compositions as described herein may be administered to a mammal that may not have a disease or symptoms of a disease associated with NK3 activity but may be administered to antagonize NK3 along with the other physiological results described herein.

As used in the claims below and throughout this disclosure, the phrase "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of a composition" for the treatment of a particular disease or disorder, or the maintenance of a healthy condition, would exclude other ingredients that would materially alter the intended outcome of the curcumin composition.

As used herein, the meaning of the term "hot flash" would immediately be envisaged by the skilled artisan. The etiology of hot flashes would be understood by the skilled artisan to refer to the sudden feeling of warmth, usually most intense over the face, neck, and chest, and profuse sweating, which is most commonly due to menopause. However, compositions described herein can also be administered to treat, ameliorate, prevent, or reduce the effects of hot flashes that are not caused by menopause.

As used herein, a composition that "substantially" comprises a compound means that the composition contains more than about 80% by weight, more preferably more than about 90% by weight, even more preferably more than about 95% by weight, and most preferably more than about 98% by weight of the compound.

The term "pharmaceutical formulation", "formulation", "composition" and the like can refer to preparations which are in such a form as to permit the biological activity of the active ingredients to be effective, and therefore may be administered to a subject for therapeutic use along with dietary and/or nutritional supplement use. The meaning of these terms will be clear to the skilled artisan based upon the context in which they are used.

A "therapeutically effective amount" as used herein includes within its meaning a non-toxic but sufficient amount of a compound active ingredient or composition comprising the same for use in the embodiments disclosed herein to provide the desired therapeutic effect. Similarly, "an amount effective to" or "an effective amount" as used herein includes within its meaning a non-toxic but sufficient amount of a compound active ingredient or composition comprising the same to provide the desired effect. A "therapeutically effective amount" or an "effective amount" includes amounts of compounds that would not be achievable through a standard diet, but requires supplementation and dosing as described herein. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it may not always be possible to specify an exact "effective amount." However, for any given case, an appropriate "effective amount" may be determined by one of ordinary skill in the art in view of the disclosure contained herein. In some aspects, a therapeutically effective amount may include a dosing regimen. For example, a therapeutically effective amount may include about 100 mg of a curcumin composition orally consumed each day for fourteen consecutive days. In some aspects, a therapeutically effective amount may include about 100 mg of a composition orally consumed each day for thirty consecutive days. Compositions including a composition may include, for example, between 0.1-1000 grams of the composition.

As used herein, the terms "synergy", "synergistic", "synergism" and the like are used herein to generally refer to the therapeutic efficacy of the composition being at least equal to the sum of the efficacy of the individual components in the composition administered independently. "Synergy", "synergistic", "synergism" and the like may also refer to the therapeutic efficacy of a composition being greater than the sum of the efficacy of the individual components in the composition administered independently. The scopes and meanings of which will be clear to the skilled artisan based upon the context in which these terms are used.

As provided herein, the disclosure of a "ratio" of compounds and compositions corresponds to a ratio provided in terms of mass of the components present in the ratio.

As used herein, the term "pharmaceutically acceptable solvent" can refer to water, water for injection, aqueous buffer solutions that are physiologically compatible, or aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents,"December 1997 or its current issue.

As used herein, the term "bioavailability" refers to the amount of a substance that is absorbed in the intestines and ultimately available for biological activity in a subject's tissue and cells.

As used herein, the term "enhancing the bioavailability" and the like are used herein to refer to obtaining a desired pharmacological and/or physiological effect of antagonizing NK3 that is absorbed from the intestine or is taken up by tissues and cells after administration of a composition to a mammal, which does not occur naturally. The effect may be prophylactic in terms of preventing or partially preventing the incidence, risk, or severity of an adverse symptom or condition caused by or related to the deficiency of a therapeutic agent.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

For the purpose of this disclosure, a warm-blooded animal is a member of the animal kingdom which includes but is not limited to mammals and birds. In certain embodiments described herein, a mammal may, for example but without limitation, be a horse, dog, or cat. The most preferred mammal of this application is a human.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

While the present invention has been described in some detail for purposes of clarity and understanding, one will appreciate that various changes in form and detail can be made without departing from the true scope of the invention.

EXAMPLES

Example 1

Method

Figure 1B:
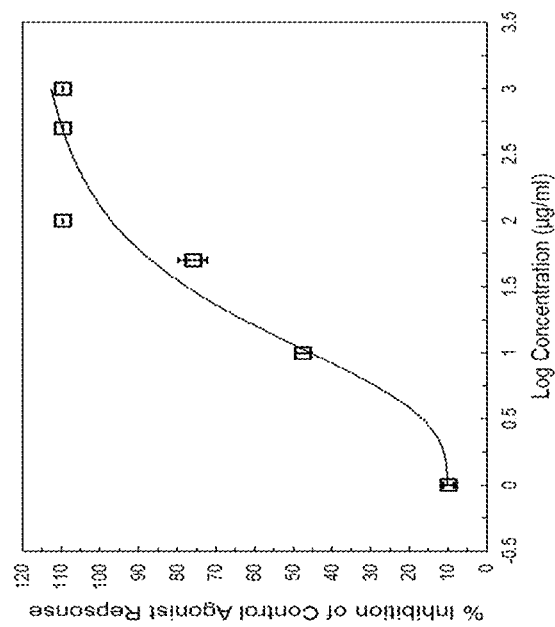
FIG. 1B shows the dose response curve of a green tea extract composition, as described herein, which was administered to transfected Chinese Hamster Ovary (CHO) cells in vitro.
Figure 1C:
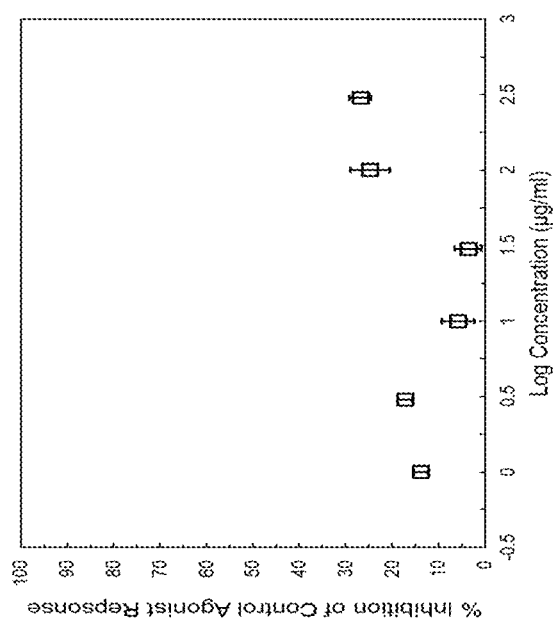
FIG. 1C shows the dose response curve of a phycocyanin composition, as described herein, which was administered to transfected Chinese Hamster Ovary (CHO) cells in vitro.

The NK3 antagonistic activity of compositions disclosed herein were studied at the human NK3 receptor expressed in transfected CHO cells. The antagonistic activity was determined by measuring their effect on Neurokinin B (NKB, a potent NK3 agonist)-induced cytosolic $Ca^{2+}$ion mobilization using a fluorometric detection method. Several ingredients were administered to transfected CHO cells, the results of which are shown in FIGS. 1A-1C, and described further below.

Experimental Protocol

The CHO cells were suspended in DMEM buffer (Invitrogen) complemented with 0.1% FCSd, then distributed in microplates at a density of $3\times10^4$ cells/well. The fluorescent probe (Fluo4 Direct, Invitrogen) was mixed with probenecid in HBSS buffer (Invitrogen) complemented with 20 mM HEPES (Invitrogen) (pH 7.4) is then added into each well and equilibrated with the cells for 60 min at 37° C. then 15 min at 22° C.

Thereafter, the assay plates were positioned in a microplate reader (CellLux, PerkinElmer) which was used for the addition of the test items, curcumin extract as defined herein, or HBSS buffer, followed by the addition (5 min later) of 1 nM [MePhe7]-NKB or HBSS buffer (basal control). Next, the changes in fluorescence intensity was determined which varies proportionally to the free cytosolic $Ca^{2+}$ion concentration. The standard reference antagonist is SB 222200, which was tested at several concentrations to generate a concentration-response curve from which its IC50 value is calculated.

The results are expressed as a percent inhibition of the control response to 1 nM [MePhe7]-NKB as shown in FIGS. 1A-1C upon administration of a curcumin composition, a green tea extract composition, and a phycocyanin composition, as described herein, respectively. FIGS. 1A-1C show superior and unexpected NK3 inhibition achieved by administration of various compounds, including a curcumin composition (FIG. 1A), a green tea extract composition (FIG. 1B), and a phycocyanin composition (FIG. 1C), expressed as the IC50 (μg/mL), and were 2.92 μg/ml, 16.9 μm/ml, and no IC50 value for the phycocyanin composition was obtained, respectively.

Example 2

Method

In vivo experiments were performed to evaluate the efficacy of a curcumin composition, a green tea extract composition, a phycocyanin composition, and the combination thereof as NK3 antagonists, by measuring hypothalamic levels of NKB.

Experimental Procedure

Female Wistar rats were purchased from Japan SLC Inc. (Shizuoka, Japan). At the age of 8 weeks, rats were ovariectomized or given a sham operation (control) under isoflurane anesthesia. All animals were individually housed under clean conditions with controlled temperature, humidity, and light (12-hr light-dark cycle) and provided a standard commercial diet and water ad libitum. All animal experimental procedures were approved by the Institutional Animal Care and Use Committee of Tsukuba Research Center of Astellas Pharma Inc., which is accredited by the Association for Assessment and Accreditation of Laboratory Animal Care (AAALAC) International. Animals were handled and cared for in accordance with the Guide for the Care and Use of Laboratory Animals.

Four weeks after surgery rats are randomly divided into 6 groups: sham-operated rats treated with a vehicle consisting of 0.5% methylcellulose solution (C); ovariectomized rats treated with a vehicle consisting of 0.5% methylcellulose solution (OVX); and ovariectomized rats treated with 600 mg HED of a curcumin composition, as described herein (OVX+CL); 300 mg HED of a green tea extract composition, as described herein (OVX+EGCG); 100 mg HED of a phycocyanin composition, as described herein (OVX+P); and a combination composition, as described herein, comprising 600 mg HED of a curcumin composition, as described herein, 300 mg HED of a green tea extract composition, as described herein, 100 mg HED of a phycocyanin composition, as described herein (OVX+CL+ EGCG+P). Vehicles or active drugs were administered for 8 days.

Body weight and food intake were measured twice: before the first administration and on the final day of administration day. At day 5 of repeated administration, one small temperature data logger (Thermochron SL, KN Laboratories Inc., Osaka, Japan) was surgically implanted into the abdominal cavity under isoflurane anesthesia and another was attached to the skin of the tail using surgical tape and a handmade aluminum protector to prevent detachment. At day 7 of repeated administration, core, skin, and room temperatures were measured every 30 min for 24 hr. Two to five hours after the final drug administration (10:00-14:00), blood samples were collected from the abdominal vena cava under isoflurane anesthesia and the uterus was isolated and weighed. Blood samples were centrifuged, and plasma was separated and stored at −80° C. until assay. Blood samples were analyzed for (i) serum levels of glucose, triglycerides, cholesterol, aspartate aminotransferase (AST), alanine aminotransferase (ALT), urea, creatinine, malondialdehyde (MDA), antioxidant enzymes such as superoxide dismutase (SOD), catalase (CAT), and glutathione peroxidase (GSHPx), curcuminoids, EGCG, and phycocyanin extracts; (ii) calcium (Ca), inorganic phosphorus (P), and alkaline phosphatase (ALP); and (iii) plasma hormone levels such as estradiol, LH, FSH, progesterone and testosterone, according to known methods in the art.

Brain tissue analysis was performed to evaluate levels of kisspeptin, NKB, GnRH, transient receptor potential cation channel subfamily V member 1 (TrpV1), and protein c-fos. Brain tissues were embedded in paraffin, and hypothalamic slices (3-μm thickness) containing the MnPO were prepared according to a rat brain atlas (Paxinos and Watson, 2007) and standard procedures. After deparaffinization, the sections were incubated with Immunosaver (Nis shin EM Co., Ltd., Tokyo, Japan) at 100° C. for 15 min for antigen retrieval followed by 3% hydrogen peroxide to block endogenous per-oxidases. The samples were incubated with 1% bovine serum albumin for 20 min at room temperature followed by anti-kisspeptin, NKB, GnRH, TrpV1, or c-fos monoclonal antibody (dilution 1:100) overnight at 4° C. The samples were then treated with the DAKO EnVision System (Agilent Technologies, Santa Clara, CA, USA). ImmPACT DAB (Vector Laboratories, Inc., Burlingame, CA, USA) was used for color development. The densitometric analysis of the relative intensity according to the control group of the western blot bands was performed with (3-actin normalization to ensure equal protein loading. Blots were repeated at least three times (n=3) and a representative blot is shown. ANOVA and Tukey's post-hoc test were performed for statistical comparisons (p<0.05). Data are presented as mean ±standard deviation. Different lowercase letters above data series (a-d) indicate a statistical difference between groups.

Quantitative assessment of c-Fos--positive neurons (stained-reddish-brown) was performed using a computerized image analysis system (WinROOF Ver. 6.0; Mitani Corp., Fukui, Japan) to automatically (optimal color wavelength and approximate cell size were entered in advance) count the number of reddish-brown (c-Fos-positive) cells in the MnPO under light microscopy at a magnification of 100x.

Figure 2:
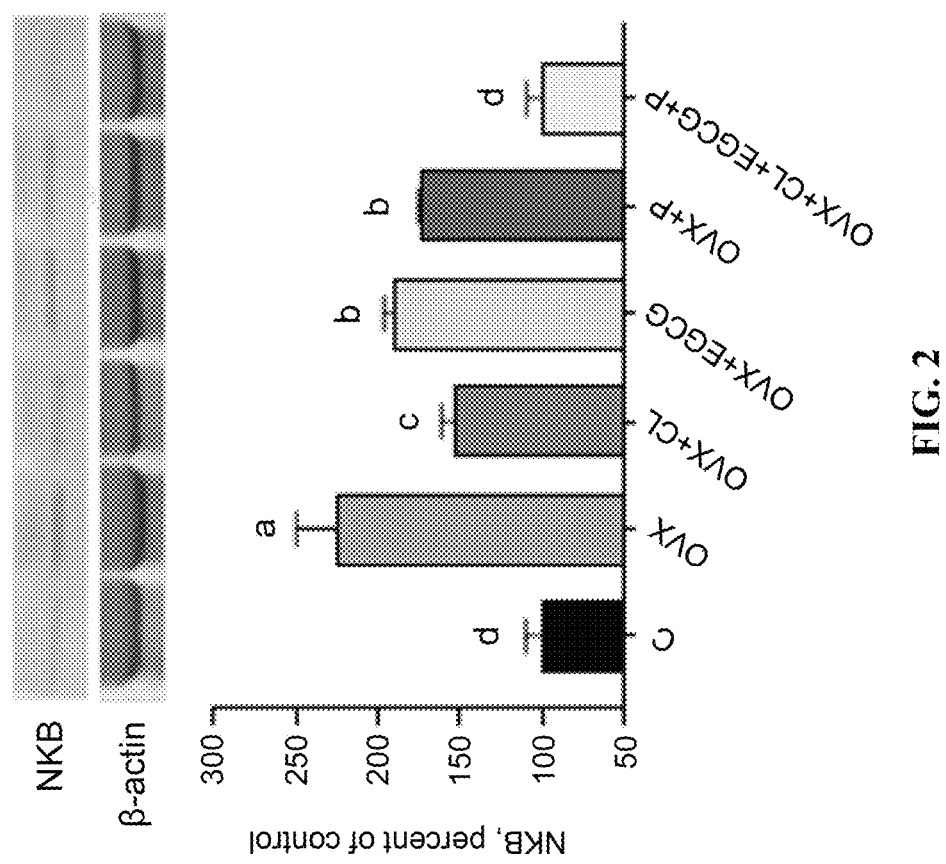
FIG. 2 shows the results of administration of a curcumin composition, a green tea extract composition, and a phycocyanin composition, and the combination thereof administered to female Wistar rats in vivo.

Results of hypothalamus levels of NKB following the treatment scheme of Example 2 are shown in FIG. 2. FIG. 2 shows superior and unexpected results. As expected, rats receiving the ovariectomy treatment (OVX), demonstrated the highest levels of NKB hypothalamus levels. Surprisingly, individual compositions according to the disclosure, significantly reduced NKB levels, below that of the OVX rats. Unexpectedly, a combination composition, as described herein (OVX+CL+EGCG+P), returned NKB levels to those seen in non-ovariectomized mice receiving a saline treatment (C).

Example 3

Method

In vivo experiments were performed to evaluate the efficacy of combination compositions, of the disclosure, comprising a curcumin extract composition, a green tea extract composition, and a phycocyanin composition of the disclosure, as NK3 antagonists, by measuring hypothalamic levels of NKB.

Experimental Procedure

The experimental procedure of Example 3 is the same procedure and analysis as described in Example 2. In Example 3, various combination compositions, as disclosed herein, comprising varied amounts of a curcumin composition, a green tea extract composition, and a phycocyanin composition according to the disclosure. In Example 3, the experimental groups were: sham-operated rats treated with a vehicle consisting of 0.5% methylcellulose solution (C); ovariectomized rats treated with a vehicle consisting of 0.5% methylcellulose solution (OVX); ovariectomized rats treated with 600 mg HED of a curcumin composition, 300 mg HED of a green tea extract composition, 100 mg HED of a phycocyanin composition (OVX+CL1+EGCG1+P); 450 mg HED of a curcumin composition, 450 mg HED of a green tea extract composition, 100 mg HED of a phycocyanin composition (OVX+CL2+EGCG2+P); and 720 mg HED of a curcumin composition, 180 mg HED of a green tea extract composition, 100 mg HED of a phycocyanin composition (OVX+CL3+EGCG3+P). Vehicles or active drugs were administered for 8 days. Data are presented as mean ± standard deviation. Different lowercase letters above data series (a-d) indicate a statistical difference between groups.

Figure 3:
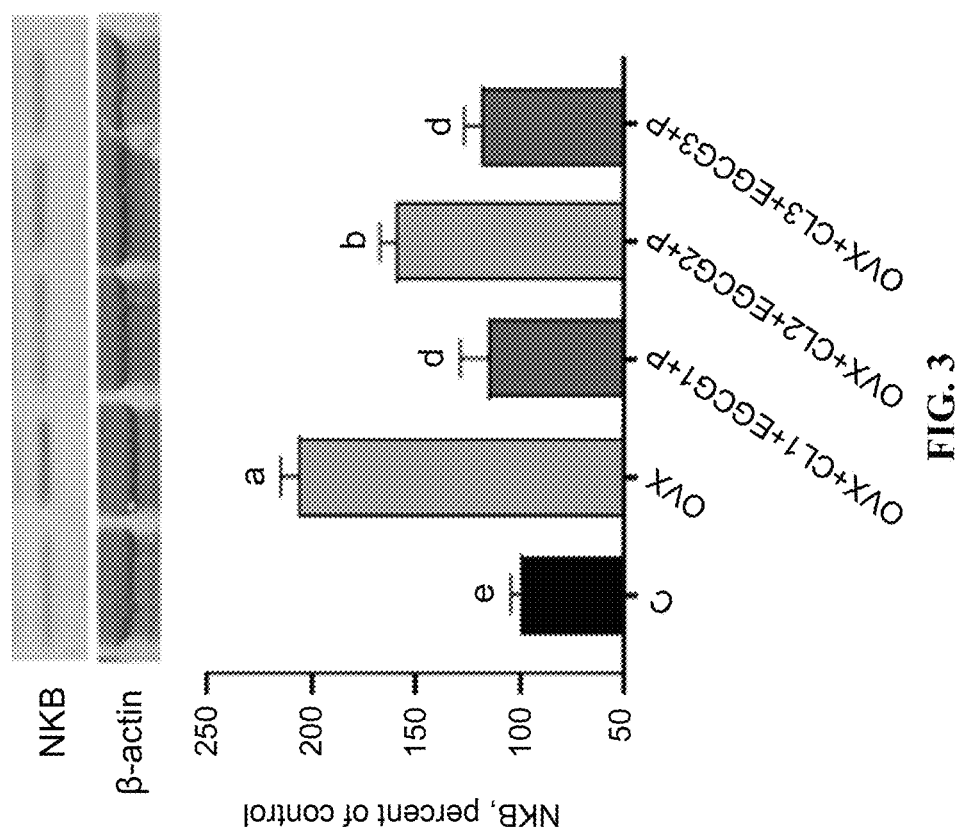
FIG. 3 shows the results of administration of combinations of a curcumin composition, a green tea extract composition, and a phycocyanin composition, as described herein, to female Wistar rats in vivo, wherein the dosages of the curcumin composition and green tea extract composition were varied.

Results of hypothalamus levels of NKB following the treatment scheme of Example 2 are shown in FIG. 3. FIG. 3 shows superior and unexpected results. As expected, rats receiving the ovariectomy treatment (OVX), demonstrated the highest levels of NKB hypothalamus levels. Surprisingly, all of the combination compositions evaluated, significantly reduced NKB levels, below that of the OVX rats.

The invention claimed is:

1. A method of treating, ameliorating, preventing, or reducing symptoms associated with menopause in a subject, the method comprising:
   identifying that the subject is experiencing or will experience symptoms associated with menopause; and
   administering a combination composition to the subject, wherein the combination composition comprises a neurokinin 3 (NK3) antagonist containing a combination of an amount of the curcumin composition, an amount of the green tea extract composition, and an amount of the phycocyanin composition in a synergistic ratio.

2. The method of claim 1, wherein the amount of the curcumin composition is about 100 mg to about 750 mg.

3. The method of claim 1, wherein the amount of the green tea extract composition is about 100 mg to about 500 mg.

4. The method of claim 1, wherein the amount of the phycocyanin composition is about 100 mg.

5. A method of treating, ameliorating, preventing, or reducing effects of hot flashes in a subject, the method comprising:
   identifying that the subject is experiencing or will experience effects of hot flashes; and
   administering a combination composition to the subject, wherein the combination composition comprises a NK3 antagonist containing a combination of an amount of the curcumin composition, an amount of the green tea extract composition, and an amount of the phycocyanin composition in a synergistic ratio.

6. The method of claim 5, wherein the amount of the curcumin composition is about 100 mg to about 750 mg.

7. The method of claim 5, wherein the amount of the green tea extract composition is about 100 mg to about 500 mg.

8. The method of claim 5, wherein the amount of the phycocyanin composition is about 100 mg.

* * * * *